United States Patent [19]

MacDonald et al.

[11] 4,273,637
[45] Jun. 16, 1981

[54] PRESSURE BALANCED EXTERNAL REFERENCE ELECTRODE ASSEMBLY AND METHOD

[75] Inventors: Digby D. MacDonald, Columbus, Ohio; Arthur C. Scott, Cupertino, Calif.

[73] Assignee: Electric Power Research Institute, Inc., Palo Alto, Calif.

[21] Appl. No.: 114,618

[22] Filed: Jan. 23, 1980

Related U.S. Application Data

[63] Continuation-in-part of Ser. No. 13,621, Feb. 21, 1979, abandoned.

[51] Int. Cl.³ .............................................. G01N 27/30
[52] U.S. Cl. ................................................ 204/195 F
[58] Field of Search ........................... 204/195 F, 1 H; 324/438

[56] References Cited

U.S. PATENT DOCUMENTS

3,463,717  8/1969  Koopman .................... 204/195 F

FOREIGN PATENT DOCUMENTS

678648  9/1952  United Kingdom ................ 204/195 F
952862  3/1964  United Kingdom ................ 204/195 F Primary Examiner—G. L. Kaplan
Attorney, Agent, or Firm—Flehr, Hohbach, Test

[57] ABSTRACT

A system for measuring the potential between a working electrode in a pressurized, high temperature environment containing a solution which supports electrolytic conduction and a reference electrode is disclosed herein. This system utilizes an external reference electrode assembly which includes a particular technique of balancing its own internal pressure with the pressure in the high temperature environment in order to eliminate streaming potentials between the working electrode and the reference electrode. This assembly also includes a technique for maintaining the concentration of electrolytic solution at a substantially fixed and uniform level so as to maintain a fixed thermal liquid junction.

16 Claims, 3 Drawing Figures

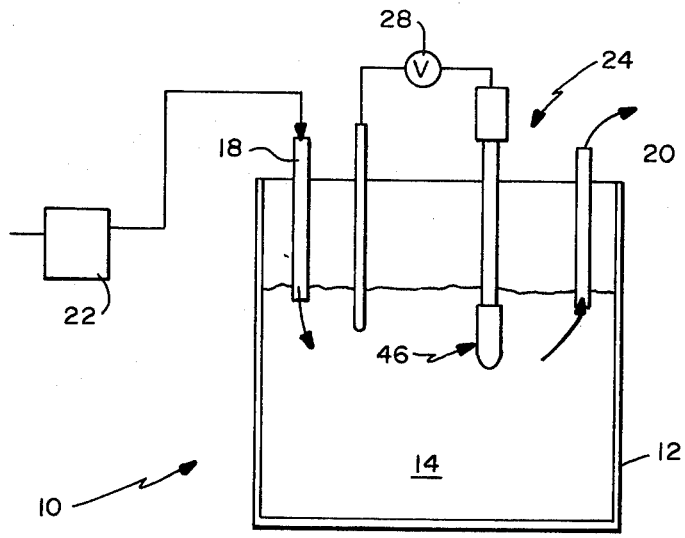
FIG.—1
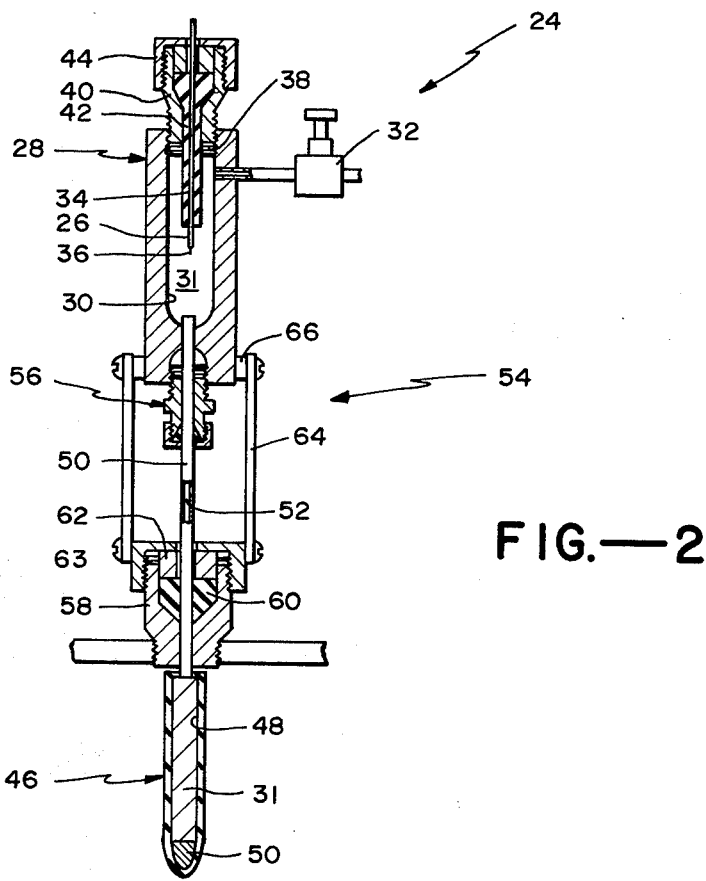
FIG.—2

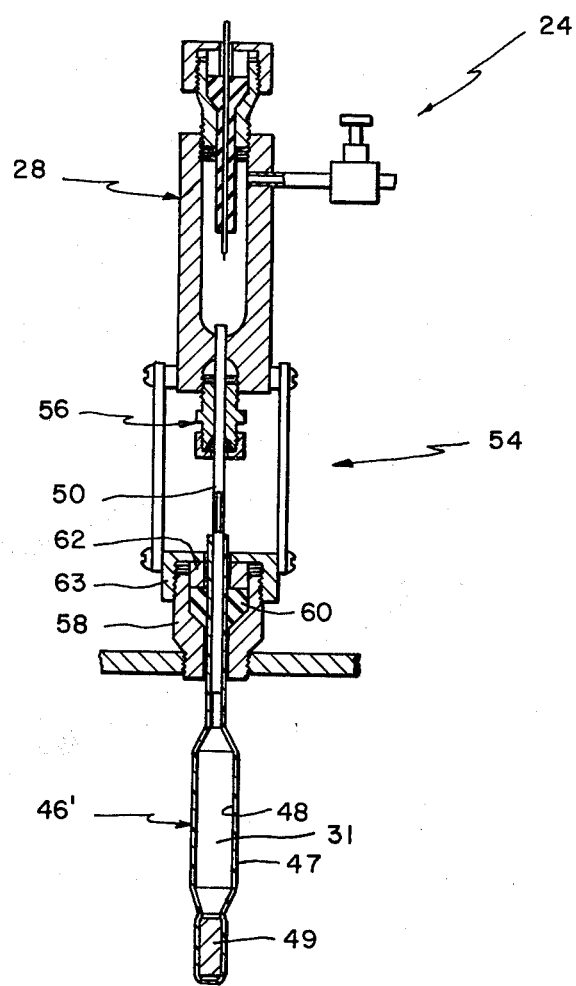
FIG.—3

PRESSURE BALANCED EXTERNAL REFERENCE ELECTRODE ASSEMBLY AND METHOD

This application is a continuation-in-part of U.S. patent application Ser. No. 013,621 filed Feb. 21, 1979 and now abandoned.

The present invention relates generally to reference electrode in high temperature agueous systems and more particularly to an external reference electrode assembly which eliminates streaming potentials and, in a preferred embodiment, also maintains a fixed thermal liquid junction regardless of the tendency to establish a thermal diffusion gradient.

Recent interest in the electrochemistry and corrosion behavior of metals and alloys in pressurized, high temperature agueous systems has stimulated research into the design of reliable reference electrodes for use in this hostile environment. Much of the recent effort has been directed towards developing internal reference electrodes that operate at the temperature and pressure of the system. However, few internal electrodes are sufficiently stable for use at temperatures above 250° C. for extended periods of time. The principal problem is hydrothermal hydrolysis, although parasitic processes such as the $H_2/H^+$ reaction may also interfere with the proper operation of the reference electrode. The problems encountered with the use of internal reference electrodes have been extensively reviewed in an article entitled *"Reference Electrodes for High Temperature Aqueous Systems—A Review and Assessment"*, by Digby D. Macdonald, in CORROSION, Vol. 34, No. 3, pp. 75–84 (1978) March and reference is made thereto. External reference electrodes which are housed in separate compartments that are maintained at ambient temperatures are attractive alternatives to internal reference electrodes. This approach has the advantage of not being limited by elevated temperatures and the reference electrode itself need only be compatible with its surrounding electrolytic solution. An assembly of this general type typically includes a first outer housing which is located outside the hostile environment and which defines an inner chamber filled with electrolytic solution, for example, potassium chloride (KCl). The reference electrode itself is contained in the electrolytic solution within this chamber and is adapted for connection with a voltmeter along with the working electrode for measuring the potential between the two. This typical assembly also includes a second inner housing which is located within the hostile environment and which defines its own inner chamber filled with electrolytic solution. These two chambers are placed in fluid communication with one another by an alumina tube or other suitable means which defines a passageway therebetween and which establishes a temperature gradient along its length. A liquid junction, for example, zirconium oxide ($ZrO_2$), porous alumina, asbestos or the like is interposed between the hostile environment and the chamber within the inner housing for providing an electrolytic conduction path between the two solutions (which are generally different) while preventing gross mixing of the two.

It should be apparent from the foregoing that the chambers within the external reference electrode assembly thus far described are not necessarily at the same pressure as the pressurized, high temperature environment being evaluated. In fact, unless compensated for, the chambers within the electrode assembly are at ambient pressure whereas the environment being evaluated is at a substantially higher pressure, for example, 1,000 psi. This, of course, creates a pressure gradient between the two resulting in what is commonly referred to as "streaming potentials", the presence of which is detrimental to the true evaluation of the potential between the working and reference electrodes.

In the previously recited article by Macdonald, an external reference electrode assembly is described wherein the external pressure surrounding the reference electrode, that is, the pressure within the outer housing, is matched with the internal pressure of the system, that is, the pressure within the hostile environment, thereby eliminating streaming potentials. However, this is accomplished in a rather complicated, inconvenient way, specifically by injecting an external supply of pressurized gas into the outer housing or removing it therefrom.

It should also be apparent from the foregoing that the temperature within the outer housing chamber containing the reference electrode is quite different than the temperature within the environment being evaluated which, of course, is the main advantage in using an external assembly.

However, this difference in temperature tends to establish thermal diffusion (the SORET effect) which takes place between the hot and cold ends of the chamber connecting tube. This, in turn, tends to change the concentration level of the electrolyte solution surrounding the reference electrode and also gives rise to a thermal liquid junction potential along the tube. While the mere presence of this potential is not detrimental to the true evaluation of the potential between the working and reference electrodes so long as it is maintained at a fixed level, it is detrimental when allowed to fluctuate as described.

Heretofore, the presence of spurious thermal liquid junction potentials in an assembly of the type described has been ignored, for the most part. However, applicants have found it to be not only desirable but of substantial benefit to relate the potential measured between the working electrode and reference electrode with a theoretical, standard scale, specifically, with what is referred to as the standard hydrogen electrode (SHE) scale. However, in order to do this, it is important not only to eliminate streaming potentials but it is also necessary to maintain a fixed thermal liquid junction potential. As will be seen hereinafter, the present invention does both in an uncomplicated and economical way.

In view of the foregoing, one object of the present invention is to provide an external reference electrode assembly of the general type described but one which eliminates streaming potentials in an uncomplicated, economical and reliable way.

Another object of the present invention is to provide an external reference electrode assembly which maintains a constant thermal liquid junction potential regardless of the tendency of thermal diffusion to occur.

Still another object of the present invention is to provide an external reference electrode assembly which is capable of measuring the potential between a working electrode in the hostile environment described and an external reference electrode in terms of the SHE scale.

Other objects and features of the present invention will become apparent hereinafter from the detailed description to follow. As will be seen then, the external reference electrode assembly disclosed herein measures the potential between a working electrode in a pressurized, high temperatures environment containing a solution which supports electrolytic conduction and a reference electrode utilizing many of the components described previously. Among these components is a housing means including an overall chamber which is filled with electrolytic solution and which may be separated into an inner chamber section within the high temperature environment, an outer chamber section outside this environment, and an intermediate chamber section along which a temperature gradient between the inner and outer sections is established. A liquid junction in the housing means provides an electrolytic path between the two solutions, that is, between the solution in the high temperature environment and the solution in the inner chamber. A reference electrode is contained within the outer chamber and is adapted for connection to a voltmeter along with the working electrode for measuring the potential therebetween.

In accordance with one aspect of the present invention, the assembly just described includes means for varying the volume of the overall chamber containing the reference electrode in response to changes in pressure in the high temperature environment in a way which maintains the pressure within the chamber substantially equal to the pressure in the high temperature environment. This, in turn, eliminates the previously described streaming potentials. In accordance with another aspect of the present invention, the assembly just described includes means for maintaining the concentration of electrolytic solution in the chamber containing the reference electrode at a substantially fixed level regardless of the tendency to establish a thermal diffusion gradient between the inner and outer chamber sections. This, in turn, maintains a fixed thermal liquid junction potential along the length of the intermediate chamber section.

The specific way in which chamber volume is varied for balancing the pressure in order to eliminate streaming potentials and the particular way in which the assembly maintains a fixed concentration level of electrolytic solution within the assembly chamber for maintaining a fixed thermal liquid junction potential will be described hereinafter with respect to the drawing wherein:

FIG. 1 is a diagrammatic illustration of a pressurized, high temperature environment containing a working electrode within a solution which supports electrolytic conduction and an external reference electrode assembly for measuring the potential between the working electrode and a reference electrode located outside the environment;

FIG. 2 is an elevational view, partially in section, of at least a part of the external reference electrode assembly illustrated in FIG. 1; and FIG. 3 is a view similar to FIG. 2 illustrating a modified, preferred embodiment of the assembly of FIG. 2.

Turning to FIG. 1, a hostile environment of the general type described previously is shown diagrammatically in FIG. 1. This environment which is generally indicated by the reference numeral 10 includes a pressurized vessel 12 containing a solution 14 which is capable of supporting electrolytic conduction. This solution, which may be aqueous or non-aqueous, is maintained at a relatively high temperature, for example, as high as 300° C., resulting in relatively high pressures within the vessel, for example, on the order of 1000 psi. There are many different types of apparatus which may include such an environment including many nuclear reactors.

Each of these apparatus will also include its own working electrode 16 which may serve only as an electrode, as indicated in FIG. 1, which may be used as an electrode but which normally serves an entirely different function in the overall operation of the apparatus. In either case, the component used as the working electrode within environment 10 must be compatible with solution 14 and be made of the appropriate material to function as an electrode and must be at least partially immersed within the solution as shown. In the case of nuclear reactors, as well as other apparatus, a continuous stream of solution 14 is pumped into and out of vessel 12 through suitable inlet and outlet means 18 and 20, respectively, by means of a suitable pump 22, as indicated by the arrows in FIG. 1. This circulation system, including the inlet and outlet tubes, the pump and other components (not shown) may be conventional along with the rest of the components making up the overall apparatus. However, for reasons to be discussed hereinafter, pump 22 is preferably the positive displacement pump capable of oscillating the pressure level within vessel 12 in a predetermined way for a specific purpose. In order to evaluate certain aspects of environment 10, an external reference electrode assembly 24 designed in accordance with the present invention is used for measuring the potential between working electrode 16 and a reference electrode 26 (see FIG. 2) comprising part of assembly 24. To this end, both the working electrode and reference electrode must be connectible to a voltmeter 28 or other suitable device for measuring the potential therebetween. As indicated previously, one objective of the present invention is to relate this measured potential to a thermodynamically meaningful scale, preferably to the standard hydrogen electrode (SHE) scale. Accordingly, it might be desirable to appropriately calibrate voltmeter 28 to automatically reflect this scale. As also indicated previously, in order to use the SHE scale, it is important to eliminate streaming potentials and to prevent fluctuations in the thermal liquid junction potential. As will be seen hereinafter, assembly 24 eliminates streaming potentials by balancing its internal pressure with that of environment 10 in an uncomplicated, reliable and yet economical way and it stabilizes its thermal liquid junction potential in an uncomplicated, reliable and economical way, preferably utilizing pump 22.

Turning to FIG. 2, attention is now directed specifically to external reference electrode assembly 24. As seen in this figure, the assembly includes an outer housing 28 constructed of any suitable material such as stainless steel or like metal. This outer housing is positioned outside vessel 12, i.e., environment 10, and includes an inner chamber 30 filled with an electrolytic solution, that is, a solution capable of supporting electrolytic conduction. In a preferred embodiment, an aqueous solution of potassium chloride (KCL) is utilized at a convenient but operable level readily determined by those skilled in the art. Outer housing 28 may include a suitable bleed valve 32.

As stated previously, assembly 24 includes external reference electrode 26. This electrode may be of any suitable type, compatible with electrolytic solution 31, for providing the potential between the two electrodes. However, when electrolytic solution is KCl, electrode 26 is preferably comprised of a silver wire 34 having an outer Teflon coating and a silver wire spiral tip 36 coated with silver chloride (AgCl). The name Teflon used herein is a trademark of DuPont Company.

The electrode extends into chamber 30 from the ambient surroundings through an internally threaded opening 38 in housing 28 so that spiral tip 36 is immersed within electrolytic solution 31. The electrode is supported in this position by means of an externally threaded Conax fitting 40 which is threaded into housing opening 38 and which includes a Teflon insert 42. A top cover 44 is threaded around the top end of fitting 40 and includes a top through hole for wire 34 so that the latter can be readily connected to voltmeter 28.

Assembly 24 also includes an inner housing 46 which is positioned within solution 14 in environment 10 and which defines its own inner chamber 48 filled with electrolytic solution 31. Housing 46 also includes a conventional liquid junction 49 interposed between solution 14 in environment 10 and solution 31 in chamber 48 for providing an electrolytic conduction path between the two solutions while, at the same time, preventing mass mixing of the two. The liquid junction may be constructed of any suitable material which is compatible with the two solutions and which has the porosity to function in the intended way such as alumina and asbestos but is preferably porous zirconium oxide ($ZrO_2$). For reasons to be discussed hereinafter, the body of housing 46 is constructed of a flexible material, preferably thin Teflon tubing and dimensioned in a certain way to balance the pressure within chamber 48 with the pressure within environment 10.

The two housing chambers just described, that is, chamber 30 located within outer housing 28, and chamber 48 located within inner housing 46, are placed in fluid communication with one another by an interconnecting tube 50 extending between and connected to the two housings. This tube defines an internal passageway 52 which is placed in fluid communication with chambers 30 and 48 and which is also filled with electrolyte solution 31. The passageway is sufficiently large so as to provide uniform pressure throughout the two chambers and along its own length. The tube itself may be constructed of any dielectric material which is compatible with solution 31 and capable of establishing a temperature gradient between the two chambers along its own length. In a preferred embodiment, inner connecting tube 50 is constructed of alumina.

As seen in FIG. 2, housing 28 is supported directly above housing 46 directly over and to the top of previously recited vessel 12 by means of an overall support arrangement 54. This arrangement includes a bored-through swagelock fitting with Teflon ferrules which is generally indicated at 56 and which is provided for supporting the top end of tube 50 relative to the bottom end of housing 28. A conax (or swagelock) fitting 58 having a Teflon insert 60, Teflon packing rings 62 and a top cap 63 serve to support the bottom end of tube 50 to the top of pressure vessel 12. In most cases, the interconnecting tube will be constructed of a relatively brittle material and, hence, to protect the tube, support arrangement 54 includes a plurality of outer support rods 64 connected at their top ends with housing 28 and at their bottom ends with fitting 58. In this regard, since this latter fitting, its top cap 63, and the support rods 64 are typically metal, as is housing 28, it is important to electrically insulate the latter from vessel 12 which is also typically metal. This is accomplished by means of Teflon insulators 66 suitably connected to housing 28 between the latter and support rods 64. In this way, the top ends of the support rods can be fastened to the insulators, for example, by means of screws, rather than directly to the top housing.

Having described external reference assembly 24 from a structural standpoint, attention is now directed to the way in which this assembly operates to measure the potential between working electrode 16 and its own reference electrode 26. In this regard, it should be apparent from both FIGS. 1 and 2 that a continuous electrolytic conduction path is provided between the two electrodes. This path includes solution 14 within environment 10 and also solution 31 which fills the inner and outer housings and interconnecting tube 50. As a result, a potential is developed across these two electrodes (its level depending upon the particular makeup and concentration of the two solutions and on the properties of the electrodes) and can be measured by means of voltmeter 28. It should be noted that, unless compensated for, the pressure within environment 10 including working electrode 16 is substantially higher than the pressure within chamber 30 including the reference electrode 34. This is because the reference electrode is located outside the pressurized environment, typically at ambient pressure. However, assembly 24 is designed to maintain the pressure within chamber 30 at substantially the same high level as environment 10, even though the pressure within the latter may fluctuate as a result of changes in temperature. As will be seen below, this is accomplished in accordance with the present invention by varying the combined volume of the two chambers 30 and 48 and passageway 52 in response to changes in pressure in environment 10 in a way which maintains the pressure of the uppermost chamber, that is, chamber 30, substantially equal to the pressure in environment 10.

The combined volume just referred to could be varied by changing the volume in top chamber 30 in response to changes in pressure in vessel 12 or even by changing the volume in passageway 52. However, this would require an appropriate mechanism interconnecting housing 28 or tube 50 with vessel 12 so as to respond to internal pressure changes within vessel 12 to physically change the volume of the top chamber or passageway. However, in accordance with the present invention, the volume defined by inner chamber 48 is varied in response to changes in the pressure in environment 10 to provide the appropriate pressure balance and this is accomplished without the utilization of additional apparatus as will be seen below.

As stated previously, housing 46 is constructed of a flexible material, preferably flexible Teflon tubing. This tubing must be sufficiently flexible and of sufficient diamensions lengthwise and diametrically to contract and expand automatically in response to pressure differences between environment 10 and chamber 48 until the volume of chamber 48 changes sufficiently to balance the two pressures. Obviously, when this occurs, the tubing will no longer expand or contract and its internal volume will remain constant, so long as there is a balance in pressure. This, of course, requires that the combined volume of the two chambers and passageway be completely filled with electrolytic solution 31. In an actual working embodiment, flexible housing 46 is constructed of Teflon tubing which is about 20 mils thick and about 4 inches long from one end of its inner chamber to the other, and has an inner diameter of about $\frac{1}{4}$ inch. In one operating example of the present invention, housing 46 is positioned within an environment which is pressurized to between about 1000 and 1100 psi at a typical operating temperature of 275° C. A pressured water nuclear reactor includes such an environment.

While housing 46 eliminates streaming potentials within assembly 24 by balancing the pressure with chamber 30 with the pressure in environment 10, it does not eliminate the temperature gradient between the hot end of tube 50 and its cold end. Unless compensated for, this temperature gradient causes the concentration of an otherwise uniform electrolyte solution 31 to shift during evaluation. This in turn, results in a variable thermal liquid junction potential along the length of the tube. To make sure that this thermal liquid junction potential remains stable, that is, fixed, it is necessary to make sure that the concentration level of the electrolytic solution surrounding the reference electrode also remain uniform and fixed. In accordance with the present invention, assembly 24 accomplished this by providing means for periodically varying the combined volume of the two chambers 30 and 48 and passageway 52 a slight but sufficient amount and at sufficient time intervals to provide sufficient movement of the electrolytic solution for maintaining the concentration level substantially fixed, without destroying the temperature gradient. In the embodiment illustrated, this can be accomplished by any suitable means of periodically changing the volume of housing 46. However, in accordance with the present invention, it is accomplished by utilizing the positive displacement pump 22 which was described with respect to FIG. 1. By utilizing this type of pump to generate a stream of solution 14 into and out of environment 10, the pressure within the environment has been found to oscillate slightly above and slightly below its average level at the particular temperature in the environment. For example, when the pressure is normally at 1000 psi, for example at a temperature of 275° C., pump 22 oscillates the pressure between a value of ±20 psi. The pulses preferably take place within a frequency range of 1/second to 1 every 5 seconds. However, it is to be understood that the exact amplitude and frequency of oscillation will depend upon the particular design of assembly 24 and can be readily determined based upon the teachings herein.

In an actual working embodiment of the present invention, overall assembly 24 includes a housing 46' illustrated in FIG. 3. Otherwise, the assembly shown in this latter Figure may be identical to the assembly shown in FIG. 2.

Turning to FIG. 3, housing 46' is shown including a heat-shrinkable polytetrafluoroethylene (PTFE) tubing 47 having one end shrunk tightly around a bottom end section of alumina tube 50. The other end of the PTFE tubing is shrunk around liquid junction 49 also comprising part of the housing. The portion of PTFE tube which is shrunk around the alumina tube extends through Conax fitting 58 in order to provide an effective pressure seal between the tube and the inner liquid 31 and between the tube and solution 14.

It is to be understood that either the preferred actual working embodiment show in FIG. 3 or the embodiment shown in FIG. 2 is used for measuring the potential between the working electrode in the hostile environment and the reference electrode. Obviously, any suitable voltage measuring means may be used including, for example, means suitably calibrated to indicate the ph of the liquid in the environment.

What is claimed is:

1. An external reference electrode assembly for use in measuring the potential between a working electrode in housing means providing a pressurized, high temperature environment containing a solution which supports electrolytic conduction and a reference electrode located outside said environment, said assembly comprising: a first rigid housing adapted to be positioned outside said environment and including a first inner chamber filled with an electrolytic solution; a reference electrode located in said electrolytic solution within said chamber and adapted for connection with a voltage measuring means along with said working electrode for measuring the potential between the two electrodes; a second housing including a flexible section adapted to be positioned in its entirety within said pressurized, high temperature environment and defining a second inner chamber filled with said electrolytic solution, said second housing including a liquid junction adapted to be interposed between said environment and said second chamber for providing an electrolytic conduction path between the solutions within said environment and said second chamber; a rigid tube connected with said first and second housing and defining a passageway in fluid communication with and extending between said chambers and filled with said electrolytic solution, said tube being of a material which establishes a temperature gradient between said chambers along said passageway; and pressure control means adapted to vary the combined volume of said first and second chambers and said passageway in response to changes in pressure in said environment in a way which maintains the pressure in said first chamber substantially equal to the pressure in said environment, said pressure control means including said flexible section, the latter being sufficiently flexible to vary the volume within said second chamber depending on the pressure in said environment to provide said equal pressures.

2. An assembly according to claim 1 wherein said flexible section extends circumferentially around said second chamber.

3. An assembly according to claim 2 wherein said flexible section is constructed of polytetrafluoroethylene tubing sufficiently thin to provide the flexibility needed to equalize the pressure within said first chamber with the pressure in said environment.

4. An assembly according to claim 3 wherein said polytetrafluoroethylene tubing has one end connected around and sealed with one end of said rigid tube and an opposite end connected around and sealed with said liquid junction.

5. An assembly according to claim 4 wherein said tubing is heat shrinkable polytetrafluoroethylene which is shrunk tightly around said rigid tube and liquid junction.

6. An assembly according to claim 1 including means for maintaining the concentration of said electrolyte solution in said first chamber at a substantially fixed level regardless of the tendency to establish a thermal diffusion gradient along said tube whereby to maintain a fixed thermal liquid junction potential along said tube.

7. An assembly according to claim 6 wherein said concentration maintaining means includes means for periodically varying the combined volume of said chambers and said passageway with sufficient magnitude and at sufficient intervals to provide sufficient movement of said electrolytic solution for maintaining said concentration level substantially fixed without destroying said temperature gradient.

8. An assembly according to claim 6 wherein said concentration maintaining means includes said flexible section and means for varying the pressure of said environment in a way which expands and contracts said flexible section sufficient to provide said periodic variance in combined volume of said chambers and passageway.

9. An assembly according to claim 1 including electrically conductive means connected with said first housing for supporting the latter and said rigid tube to said environment providing means, wherein said first housing and said environment providing means are constructed of an electrically conductive material, wherein said tube is of a dielectric material and wherein said assembly includes means for electrically insulating said first housing from said supporting means whereby to eliminate spurious voltages between the two.

10. An external reference electrode assembly for use in measuring the potential between a working electrode in a pressurized, high temperature environment containing a solution which supports electrolytic conduction and a reference electrode located outside said environment, said assembly comprising: a first rigid housing adapted to be positioned outside said environment and including a first inner chamber filled with electrolytic solution; a reference electrode located in said electrolytic solution within said chamber and adapted for connection with a voltage measuring means along with said working electrode for measuring the potential between the two electrodes; a second housing adapted to be positioned within said high temperature environment and defining a second inner chamber filled with said solution, said second housing including a liquid junction adapted to be interposed between said high temperature environment and said second chamber for providing an electrolytic conduction path between the solutions within said environment and said second chamber; chamber connecting means defining a passageway in fluid communication with and extending between said chambers and filled with said electrolytic solution, said chamber connecting means establishing a temperature gradient between said chambers along said passageway; and means for maintaining the concentration of said electrolyte solution in said first chamber at a substantially fixed level regardless of the tendency to establish a thermal diffusion gradient along said chamber connecting means, whereby to maintain a fixed thermal liquid junction potential along said connecting means, said concentration maintaining means including means for periodically varying the combined volume of said chambers and said passageway with sufficient magnitude and at sufficient intervals to provide sufficient movement of said electrolytic solution for maintaining said concentration level substantially fixed without destroying temperature gradient.

11. An assembly according to claim 10 wherein said second housing includes a flexible section and wherein said concentration maintaining means includes said flexible section and means for varying the pressure of said environment in a way which expands and contracts said flexible section sufficient to provide said periodic variance in combined volume of said chambers and passageway.

12. An external reference electrode assembly for use in measuring the potential between a working electrode in electrically conductive housing means providing a pressurized, high temperature environment containing an aqueous solution which supports electrolytic conduction and a reference electrode located outside said environment, said assembly comprising: a first rigid, metal housing adapted to be positioned outside said environment and including a first inner chamber filled with an aqueous solution of potassium chloride; a reference electrode including silver chloride on a silver wire spiral located in said potassium chloride solution within said chamber and adapted for connection with a voltage measuring means such as a voltmeter along with said working electrode for measuring the potential between the two electrodes; a second housing including a flexible tube adapted to be positioned entirely within said aqueous environment and defining a second inner chamber filled with said potassium chloride solution, said second housing including a liquid junction adapted to be interposed between said aqueous environment and said second chamber for providing an electrolytic conduction path between the solutions within said environment and said second chamber; a rigid alumina tube connected with said first and second housing and defining a passageway in fluid communication with and extending between said chambers and filled with said potassium chloride solution, said tube establishing a temperature gradient between said chambers along said passageway; electrically conductive means for supporting said tube to said environment providing means, metal support means interconnecting said first housing to said last-named means; means for electrically insulating said first housing from said tube supporting means; and pressure control means adapted to vary the combined volume of said first and second chambers and said passageway in response to changes in pressure in said environment in a way which maintains the pressure in said first chamber substantially equal to the pressure in said environment when said second housing is in the latter, said pressure control means including a flexible tube forming part of said second housing, said tube being sufficiently flexible to vary the volume within said second chamber depending on the pressure in said environment to provide said equal pressures.

13. An external reference electrode assembly for use in measuring the potential between a working electrode in housing means producing a pressurized, high temperature environment containing a solution which supports electrolytic conduction and a reference electrode located outside said environment, said assembly comprising: a first rigid, metal housing adapted to be positioned outside said environment and including a first inner chamber filled with an electrolyte solution of potassium chloride solution; a reference electrode located in said electrolyte solution within said chamber and adapted for connection with a voltage measuring means along with said working electrode for measuring the potential between the two electrodes; a second housing including a flexible tube adapted to be positioned entirely within said environment and defining a second inner chamber filled with said electrolyte solution, said second housing including a liquid junction adapted to be interposed between said aqueous environment and said second chamber; a rigid electrolyte tube connected with said first and second housing and defining a passageway in fluid communication with and extending between said chambers and filled with said potassium chloride solution, said tube establishing a temperature gradient between said chambers along said passageway; electrically conductive means for supporting said tube to said environment providing means; metal support interconnecting said first housing first housing to said last-named means; means for electrically insulating said first housing from said tube supporting means; and pressure control means adapted to vary the combined volume of said first and second chambers and said passageway in respect to changes in pressure in said environment in a way which maintains the pressure in said first chamber substantially equal to the pressure in said environment when said second housing is in the latter, said pressure control means including said flexible tube forming part of said second housing, said tube being sufficiently flexible to vary the volume within said second chamber depending on the pressure in said environment to provide said equal pressures.

14. A method of eliminating streaming potentials between a working electrode and a reference electrode in a system for measuring the potential between said working electrode when the latter is in a pressurized, high temperature environment containing a solution which supports electrolytic conduction, said method comprising the steps of providing an external reference electrode assembly including a first, rigid housing defining an outer chamber filled with electrolytic solution and containing said reference electrode, a second housing including a flexible section and defining an inner chamber and a rigid tube defining an intermediate chamber and establishing a temperature gradient between the inner and outer chambers, a liquid junction interposed between said environment and said inner chamber, positioning said assembly such that said first housing is located outside said environment and said second housing is located entirely within said environment, varying the volume in said inner chamber by expanding or contracting said flexible section in order to vary the combined volume of all of said chambers in response to changes in pressure in said environment in a way which maintains the pressure within said outer chamber substantially equal to the pressure in said environment.

15. A method according to claim 14 including the step of maintaining the concentration of said electrolyte solution in said outer chamber at a substantially fixed level regardless of the presence of a tendency for thermal diffusion to occur along the length of said intermediate chamber wherein to maintain a fixed thermal liquid junction along the length of said intermediate chamber.

16. A method according to claim 15 wherein said last mentioned step includes periodically expanding and contracting said inner chamber section by periodically increasing and decreasing the pressure of said environment.

* * * * *